United States Patent [19]

Thompson

[11] Patent Number: 5,571,092
[45] Date of Patent: Nov. 5, 1996

[54] METHOD FOR HANDLING A NEEDLE

[76] Inventor: Nancy L. Thompson, 1212 Reston Ave., Herndon, Va. 22070

[21] Appl. No.: 500,637

[22] Filed: Jul. 11, 1995

Related U.S. Application Data

[63] Continuation of Ser. No. 95,537, Jul. 26, 1993, Pat. No. 5,476,452.

[51] Int. Cl.$^6$ .................................................. A61M 5/00
[52] U.S. Cl. ........................ 604/263; 604/110; 128/919; 206/363; 206/365
[58] Field of Search .................... 128/898, 917, 128/919; 206/363–370; 606/205–207, 210, 211; 604/263, 403, 93, 110, 198, 274, 171, 246, 247, 167

[56] References Cited

U.S. PATENT DOCUMENTS

| | | |
|---|---|---|
| 3,451,540 | 6/1969 | Kulischenko . |
| 4,351,434 | 9/1982 | Elisha . |
| 4,410,086 | 10/1983 | Simpson . |
| 4,488,643 | 12/1984 | Pepper . |
| 4,520,926 | 6/1985 | Nelson . |
| 4,576,211 | 3/1986 | Valentini et al. . |
| 4,600,112 | 7/1986 | Shillington et al. . |
| 4,675,006 | 6/1987 | Hrushesky . |
| 4,722,472 | 2/1988 | Bruno . |
| 4,755,170 | 7/1988 | Golden . |
| 4,801,013 | 1/1989 | Bruno . |
| 4,840,185 | 6/1989 | Hernandez . |
| 4,846,808 | 7/1989 | Haber et al. . |
| 4,862,573 | 9/1989 | Kelson et al. . |
| 4,895,346 | 1/1990 | Steigerwald . |
| 4,927,018 | 5/1990 | Yang et al. . |
| 4,927,415 | 5/1990 | Brodsky .................................. 128/919 |
| 4,929,235 | 5/1990 | Merry et al. . |
| 4,932,946 | 6/1990 | Shields . |
| 4,956,907 | 9/1990 | Bruno ........................................ 604/403 |
| 4,986,811 | 1/1991 | Thead et al. . |
| 4,986,817 | 1/1991 | Code . |
| 4,997,422 | 3/1991 | Chow et al. . |
| 5,078,694 | 1/1992 | Wallace . |
| 5,104,388 | 4/1992 | Quackenbush . |
| 5,143,414 | 9/1992 | Rosellini ................................. 604/263 |
| 5,169,393 | 12/1992 | Moorehead et al. . |
| 5,171,229 | 12/1992 | McNeil et al. ........................... 604/263 |
| 5,176,655 | 1/1993 | McCormick et al. . |
| 5,209,733 | 5/1993 | Lever et al. . |
| 5,212,362 | 5/1993 | Burden et al. ........................... 128/919 |
| 5,259,501 | 11/1993 | Withers et al. . |
| 5,267,975 | 12/1993 | Brodsky . |
| 5,305,766 | 4/1994 | Hahn ........................................ 128/919 |
| 5,312,346 | 5/1994 | Han ........................................... 604/263 |

Primary Examiner—Corrine M. McDermott
Assistant Examiner—Ronald K. Stright, Jr.
Attorney, Agent, or Firm—Merchant, Gould, Smith, Edell, Welter & Schmidt, P.A.

[57] ABSTRACT

The present invention is a kit for handling a needle. The kit comprises a shielding device, a protector, and a needle guard. The shielding device protects against needle strikes upon extraction of the needle, the protector protects against needle strikes while inserting the needle, and the guard sheathes the needle prior to use. The shielding device includes a cavity for depositing a used needle therein and a self-closing passageway which permits the needle to enter the cavity but prevents the needle from exiting the cavity. The protector comprises a ring and a shroud. The ring has a central aperture for stabilising the patient's skin and an implanted venous access device. The shroud is joined to the ring and protects the health care worker against needle strikes while inserting the needle. The needle guard comprises a barrel having a longitudinal slit therein which is separable upon insertion of the needle into the patient's skin to permit the needle guard to be shed from the needle.

8 Claims, 7 Drawing Sheets

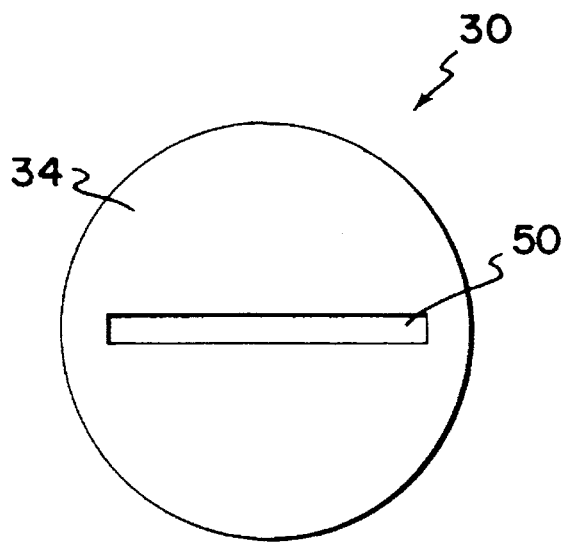
FIG. 6
FIG. 7
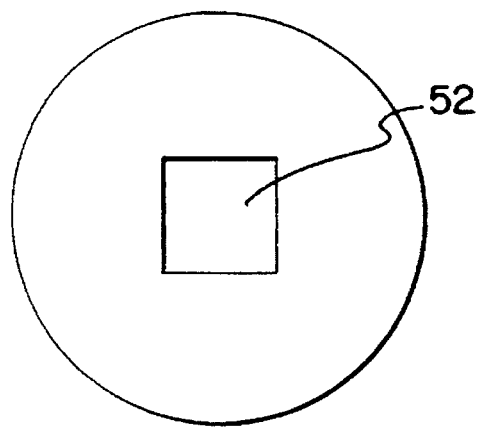
FIG. 8
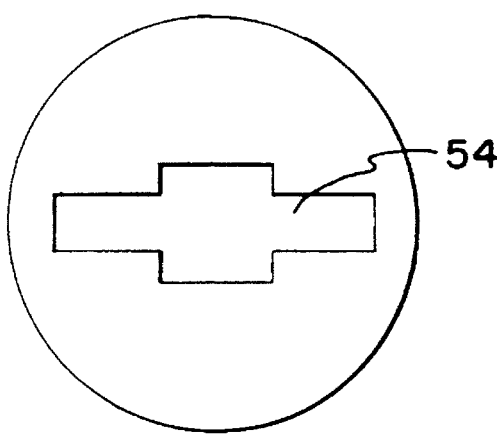

METHOD FOR HANDLING A NEEDLE

This is a continuation of application Ser. No. 08/095,537, filed Jul. 26, 1993, now U.S. Pat. No. 5,476,452, which application is incorporated herein by reference.

BACKGROUND OF THE INVENTION

1. Field of the Invention

The present invention relates to a kit for safely handling a body piercing conduit (e.g. a needle).

2. Description of the Prior Art

Intravenous therapy refers to the delivery of fluids directly into the vein. This can be accomplished through a needle or some other venous access device. Needles are generally used for short term treatments is a long term treatments which are not repeated. When the treatment is a long term treatment or is repeated, a venous access device is usually preferred. A venous access device includes a small, flexible, hollow tube, called a catheter, which is placed in a vein where it may remain for a long term. Fluid is then introduced through the catheter directly into the vein.

There are various types of venous access devices. One such device is an implantable venous access device 10, as is shown in FIGS. 15 through 18, which includes two major components, a catheter 12 and a small chamber or portal 14. In the center of the portal 14 is a self-sealing septum 16. Some implantable venous access devices have more than one portal, making it possible to introduce more than one fluid through the implantable venous access device at one time.

The implantable venous access device 10 is implanted by a doctor as follows. The catheter 12 is put through the skin S and into a vein V in the chest C of the patient P. One end 18 of the catheter 12 is threaded through the vein V to a point just above the patient's heart. The other end 20 of the catheter 12 is tunnelled a short distance. An incision is made and the portal 14 is placed under the patient's skin S. The catheter 12 is then attached to the portal 14. Upon closing the incision, the entire device 10 is concealed beneath the patient's skin S.

The implanted venous access device 10 is accessed by putting a needle 22, 24 through the patient's skin S and into the septum 16. Fluids can be introduced through the portal 14 and catheter 12 with an injection needle 22 or a needle 24 having tubing 26 attached thereto. When the implanted venous access device 10 is in use, the needle 22, 24 must be changed periodically and the patient's skin S must be cleaned about the portal 14. Each time a needle 22, 24 is removed, the healthcare worker W is subject to the risk of an accidental needle strike.

A variety of apparatuses have been devised to guard against needle strikes. For example, U.S. Pat. No. 4,927,415, issued May 22, 1990 to Stuart A. Brodsky, discloses an apparatus for preventing needle strikes. In addition to preventing needle strikes, the apparatus facilitates in the safe disposal of used, contaminated needles. The apparatus comprises a body having an entry and a closure mechanism at one end and a pulling structure passing therethrough. The pulling structure is attached to an intravenous needle. The user pulls the pulling structure to draw the needle into the body. The entry and the closure mechanism prevent the needle from exiting the body once pulled therein. Another apparatus for guarding against accidental needle strikes is disclosed in U.S. Pat. No. 4,997,422, issued Mar. 5, 1991 to Peter P. Chow et al. Chow et al. disclose a syringe with a needle guard which is slidably engageable with the syringe body for protecting against accidental needle strikes. An alternative apparatus is in U.S. Pat. No. 5,078,694, issued Jan. 7, 1992 to Henry G. Wallace, wherein a protective shield and a self-sealing diaphragm are arranged to protect a health care worker from needle strikes.

Contaminated needles offer greater exposure of accidental needle strikes to health care workers if not immediately disposed of or if improperly disposed of after use. Devices have also been devised to reduced the risk of accidental needle pricks associated with needles that have been removed from a patient after use. One such device is disclosed in U.S. Pat. No. 5,209,733, issued May 11, 1993 to Peter G. Lever et al. Lever et al. disclose an apparatus for protecting health care workers against accidental needle strikes by contaminated needles. Another apparatus associated with the disposal of contaminated needles is disclosed in U.S. Pat. No. 5,176,655, issued Jan. 5, 1993 to William McCormick et al. McCormick et al. disclose a disposable medical needle and catheter placement assembly which includes means for shielding a contaminated needle.

None of the above inventions and patents, taken either singly or in combination, is seen to describe the instant invention as claimed. Applicant's instant invention includes a shielding device which not only protects the health care worker against accidental needle strikes but also stabilizes an implanted venous access device to reduce the risk of injury to the patient upon removal of the needle.

SUMMARY OF THE INVENTION

The present invention is a kit for handling a needle. The kit is especially suitable for use with implantable venous access devices. The kit comprises a shielding device, a protector, and a guard. The shielding device includes a cover which is attached to the top end of the body. The cover has a restrictive opening which permits the passage of hemostats therethrough yet prevents the passage of a needle therethrough. A self-closing passageway is disposed interiorly of the body intermediate the cover and a lower end of the body so as to be provide a recess in the lower end of the body and a cavity between the cover and the self-closing passageway. The recess should provide suitable clearance for the portal. Both the recess and the cavity should be large enough to accommodate needles of varying sizes. The self-closing passageway includes at least one normally closed, yieldable slit. The slit is displacable so as to permit the passage of hemostats in one direction and upon grasping the needle, permit the passage of both hemostats and the needle in an opposite direction into the cavity where the needle is released by the hemostats and deposited.

The protector comprises a ring for use in stabilizing the implanted venous access device and the patient's skin. A shroud is attached to the ring for protecting a health care worker against accidental needle strikes. The ring has a central aperture for receiving and stabilizing the septum of the portal. The ring and shroud have mutually aligning, radially extending, discontinuous regions. These regions enable the protector to be removed after the needle has been inserted.

To further reduce the risk of accidental needle strikes, a needle guard is provided. The needle guard comprises an elongated, deformable barrel having a bore passing therethrough. A progressively separable, longitudinal slit is provided in the wall of the barrel. The slit originates at the lower end of the barrel and terminates a predetermined distance from the lower end. At the terminal end of the slit, an opening passes through a wall of the barrel and communicates with the bore. A needle is received by the opening and the bore. Upon insertion of the needle into the patient's skin, the slit progressively separates until the needle is completely inserted, shedding the needle guard in the process until the needle guard is completely shed from the needle.

Accordingly, it is a principal object of the invention to provide a kit, including a shielding device, a protector, and a guard, which promotes the safe extraction of a needle from and insertion of a needle into an implantable venous access device.

It is another object that the shielding device have a cover with a restrictive opening to prevent the passage of the needle therethrough, a cavity where the needle is released and deposited after use, and a self-closing passageway which permits the passage of the needle in one direction to enter the cavity yet prevents the passage of the needle in an opposite direction to retain the needle in the cavity.

It is a further object that the protector comprise a ring for stabilizing both the implanted venous access device and the patient's skin, and a shroud for protecting the health care worker against accidental needle strikes.

Still another object is that the ring and the shroud have mutually aligning discontinuous regions which enable the protector to be removed after the needle has been inserted.

Yet another object is that the needle guard sheathe the needle prior to use and that the same be deformable and include a slit which is separable upon insertion of the needle to permit the needle guard to be completely shed from the needle.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 6 shows a top adapted for use with hemostats.

FIG. 7 shows a top adapted for use with surgical tweezers.

FIG. 8 shows a top adapted for use with hemostats or surgical tweezers.

Similar reference characters denote corresponding features consistently throughout the attached drawings.

DETAILED DESCRIPTION OF THE PREFERRED EMBODIMENTS

Figure 1:
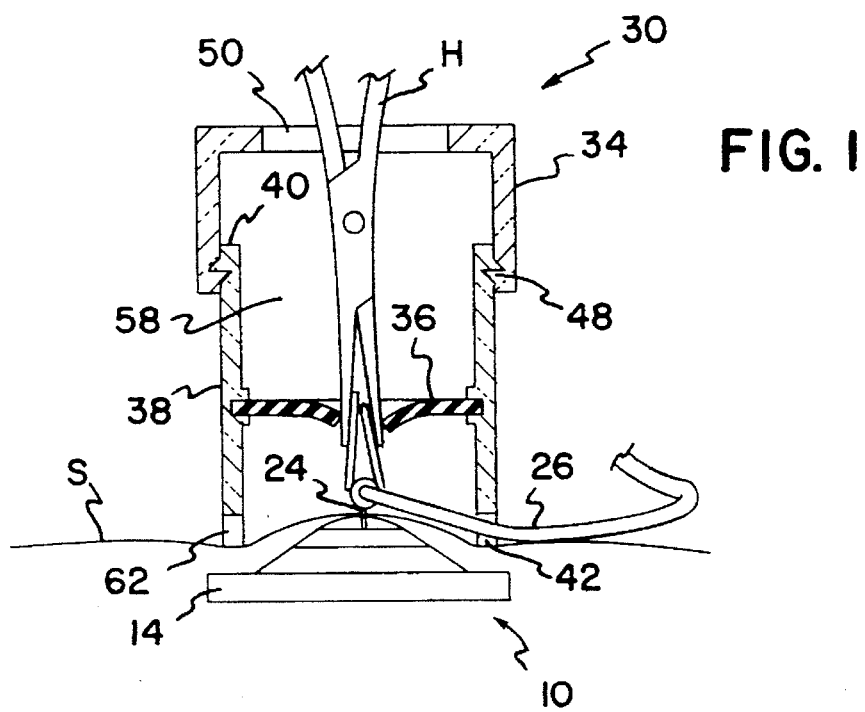
FIG. 1 is an environmental cross sectional view of a shielding device according to the present invention.

The present invention is a kit for handling needle 24. Preferably, the kit comprises three basic components: a shielding device 30; a protector 70; and a needle guard 80. The kit protects a health care worker W against accidental needle strikes upon the removal of a contaminated needle 24 from and the insertion of a needle 24 into an implanted venous access device 10. In addition, the kit stabilizes the patient's skin S as well as the implanted venous access device 10 to reduce the risk of injury and discomfort to the patient P under going treatment during the removal and insertion of a needle 24.

Figure 2:
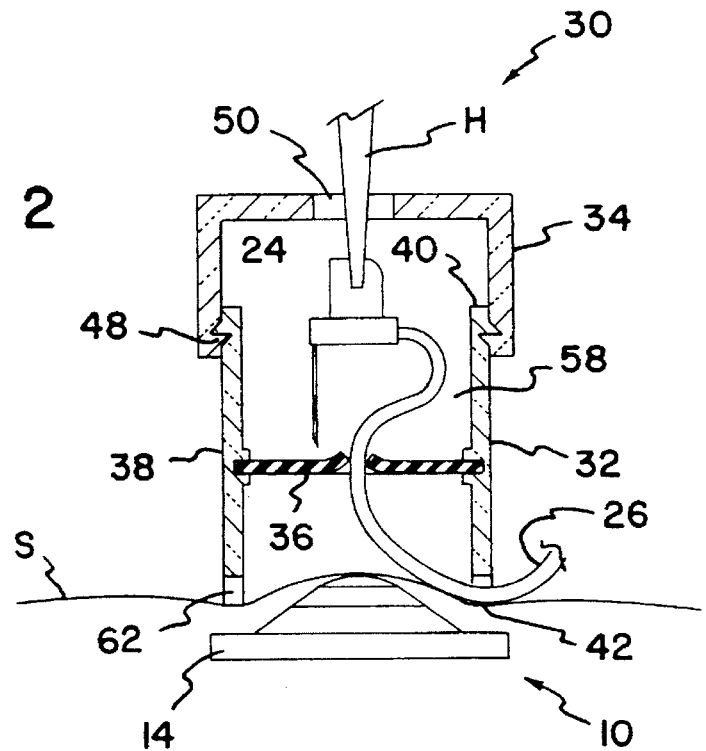
FIG. 2 is an environmental cross sectional view of the shielding device shown in FIG. 1 having a needle deposited in the cavity thereof.
Figure 3:
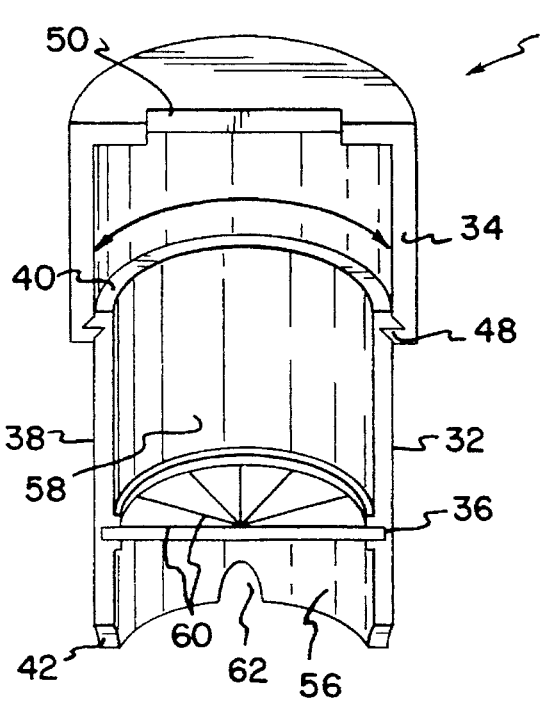
FIG. 3 is a perspective view of the shielding device shown in FIGS. 1 and 2.
Figure 4:
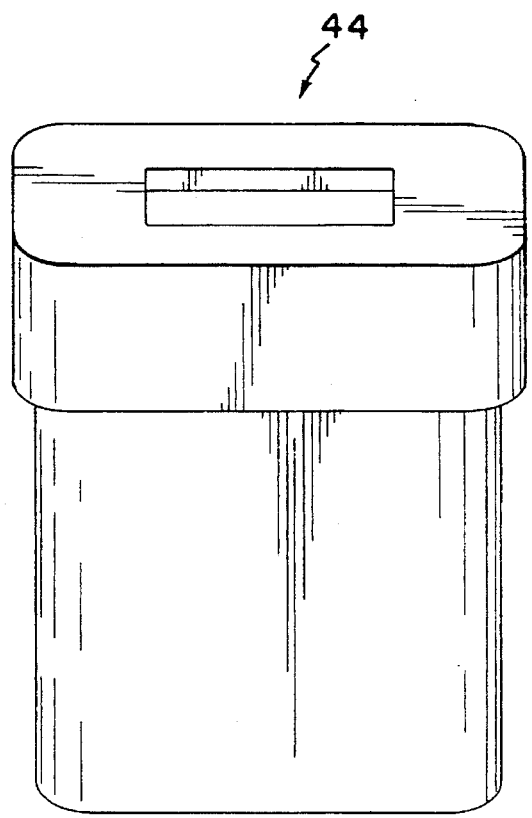
FIG. 4 is a perspective view of an alternative shielding device for use in extracting a needle.
Figure 5:
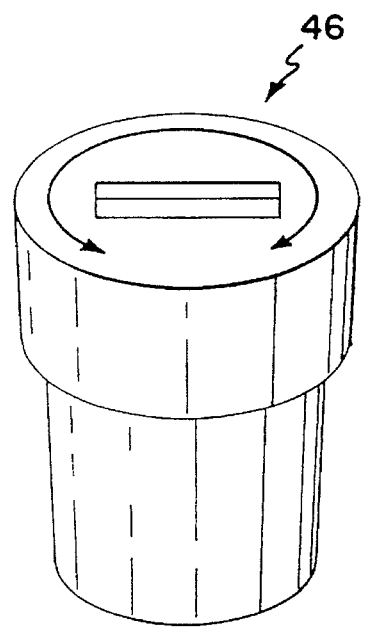
FIG. 5 is a perspective view of another alternative shielding device for use in extracting a needle.

Referring to FIGS. 1 and 2, the shielding device 30 includes a body 32, a cover 34, and a self-closing passageway 36. The peripheral walls 38 of the body 32 define the interior boundaries thereof. The body 32 includes an upper end 40 and a lower end of shoulder 42. The shoulder 42 carries dimensions slightly smaller than the dimensions of the implantable venous access device 10. Hence, the interior diameter of the body 42 should be approximately 1¾ inches to accommodate a convention portal 14. FIGS. 4 and 5 show alternative shielding devices 44, 46. One alternative shielding device 44, shown in FIG. 4, may accommodate a dual portal implantable venous access device (not shown). The other alternative shielding devices 46 is adaptable to accommodate large winged or shielded needles (neither of which are shown).

The cover 34 is disposed atop the upper end 40 of the body 32 and preferably engages the upper end 40 of the body 32 so as to permit the same to rotate relative to the body 32. The rotation of the cover 34 relative to the body 32 provides limited movement of the hemostats H passing therethrough. There should be substantially no axial movement of the cover 34 relative to the body 32. In other words, the cover 34 is preferably not removable. The cover 34 may be joined to the body 32 through a matingly engagable fastening configuration 48, as is shown in FIGS. 1 and 2, which would allow the cover 34 to snap on the body 32 and rotate but would offer resistance to the removal of the same.

The cover 34 has an opening 50 therein. The opening 50 is defined by a slot which is dimensioned and configured to permit the passage of hemostats H or locking surgical tweezers T therethrough and prevent the passage of the needle 24 therethrough. The opening 50, as is shown in FIGS. 1 through 6, may accommodate hemostats H. This opening 50 is preferably 5/16 inch wide to receive hemostats H therethrough and has a length suitably dimensioned to permit the manipulation of the hemostats H. The opening 52 shown in FIG. 7 is more suitable for surgical tweezers T. The opening 54, as is shown in FIG. 8, may accommodate either hemostats H or surgical tweezers T.

The self-closing passageway 36 is disposed interiorly of the body 32 intermediate the cover 34 and a lower end 42 of the body 32 so as to provide a recess 56 in the lower end 42 of the body 32 and bound a cavity 58 between the cover 34 and the self-closing passageway 36. Preferably, the recess 56 should be approximately ¾ inch in depth so as to provide clearance for the portal 14 and accommodate needles 24 of varying sizes. The length of the body 32 is preferably 2¼ inches or greater so as to provide the desired ¾ inch recess 56 and provide a cavity 58 large enough to receive and contain a needle 24.

The self-closing passageway 36 includes at least one normally closed, yieldable slit 60 to form a captive passage and is fabricated from a resilient material such as a hardened rubber or vinyl material. The slit or slits 60 are deformable so as to permit the passage of the hemostats H therethrough to grasp the needle 24 and upon grasping the needle 24, permit the hemostats H and the needle 24 to be pulled into the cavity 58 where the needle 24 is released by the hemostats H and the hemostats H are withdrawn through the opening 50, depositing the needle 24 in the cavity 58.

To ensure that equal pressure is applied between the shoulder 42 of the body 32 and the portal 14, at least one notch 62 is disposed in the lower end 42 of the body 32. The notch 62 permits the passage of the extension tubing 26 therethrough. Preferably, a plurality of notches 62 would be spaced equidistantly apart about the periphery of the body 32 so as to permit the pressure imposed by the body 32 against the patient's skin S and the portal 14 to be equally distributed.

In use, the hemostats H are passed downward through the shielding device 32 and clamped onto the needle 24. The portal 14 is located and the shielding device 32 is placed over the same such that the extension tube 26 passes through a notch 62. The hemostats H are pulled upward, pulling the needle 24 out of the portal 14 and through the self-closing passageway 36 and into the cavity 58. Next, the needle 24 is released from the hemostats H and the hemostats H are withdrawn from the cavity 58 through the slot 50, depositing and trapping the needle 24 in the cavity 58. The shielding device 30 may now be disposed of so as to ensure the needle 24 is rendered harmless. It is preferred that the shielding device 30, or at least the body 32, be formed of a transparent material so that the needle 24 may be observed therein.

Figure 9:
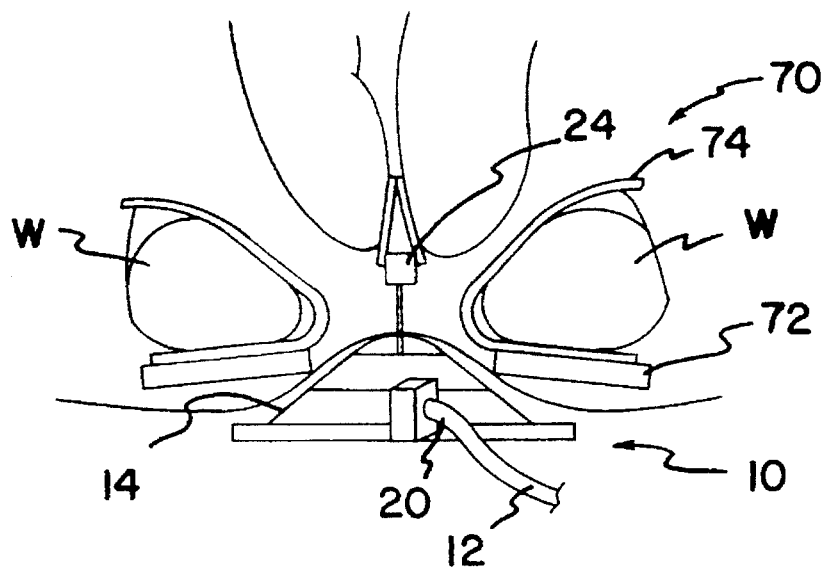
FIG. 9 is an environmental cross sectional view of a protector according to the present invention.
Figure 10:
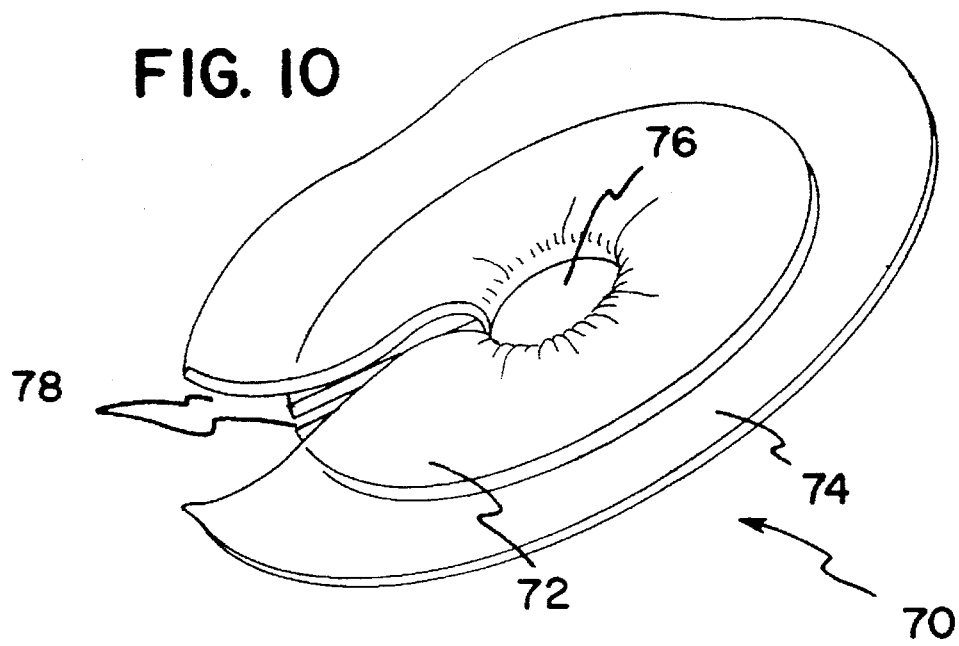
FIG. 10 is a perspective view of the protector shown in FIG. 9.
Figure 11:
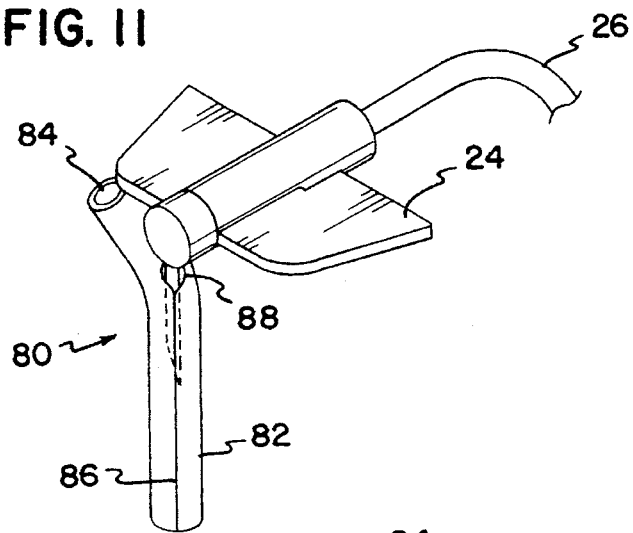
FIG. 11 is an environmental perspective view of a needle guard according to the present invention.
Figure 12:
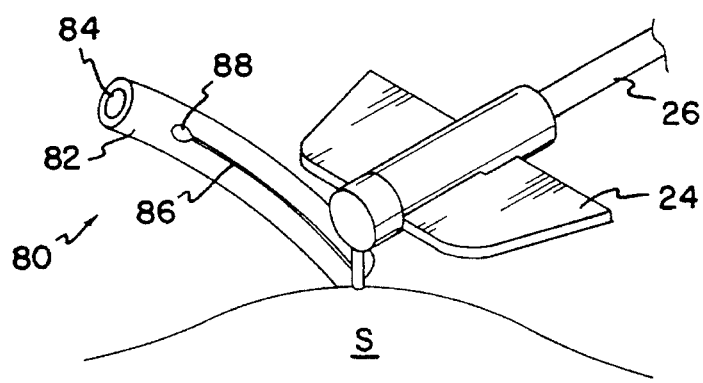
FIG. 12 is an environmental perspective view of the needle guard shown in FIG. 11 being shed from the needle.
Figure 13:
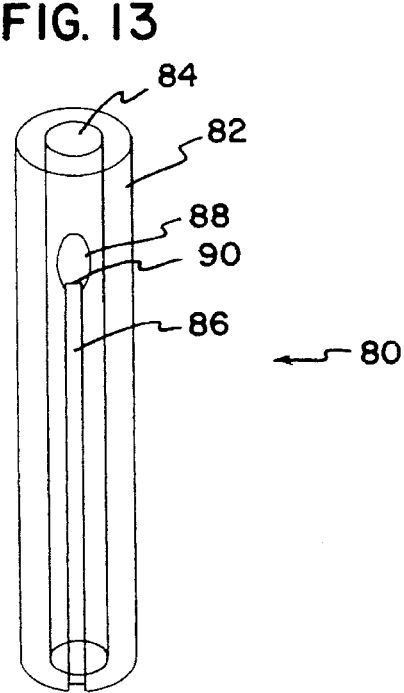
FIG. 13 is a perspective view of the needle guard shown in FIGS. 11 and 12.
Figure 14:
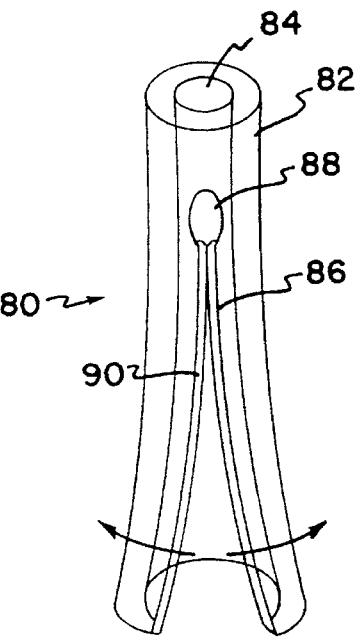
FIG. 14 is a perspective view of the needle guard showing the slit in an opened posture.
Figure 15:
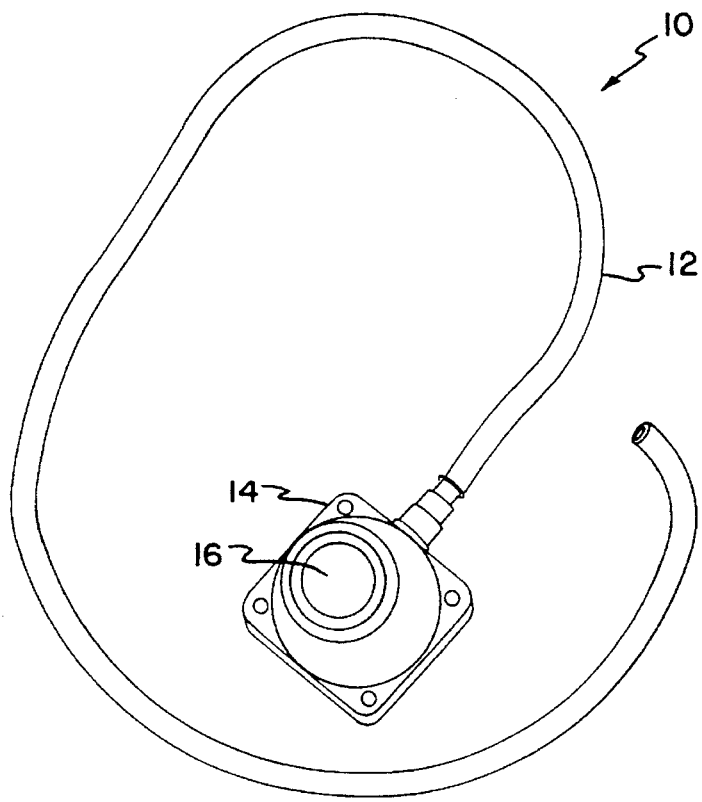
FIG. 15 is a perspective view of an implantable venous access device.
Figure 16:
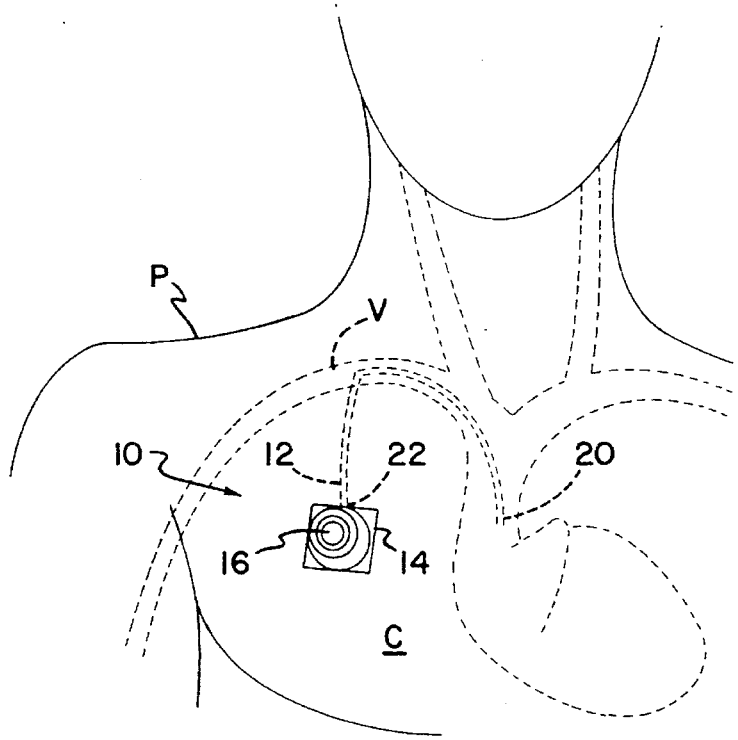
FIG. 16 is an environmental front elevational view of the implantable venous access device shown in FIG. 15.
Figure 17:
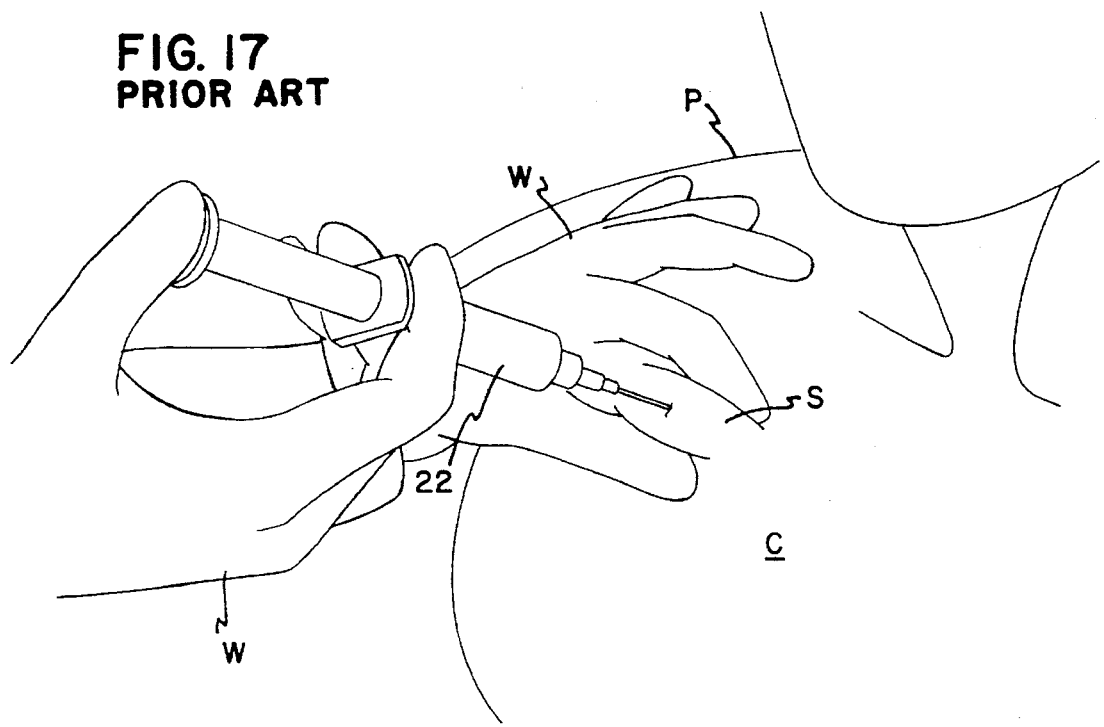
FIG. 17 is a perspective view showing access to the implantable venous access device with an injection needle.
Figure 18:
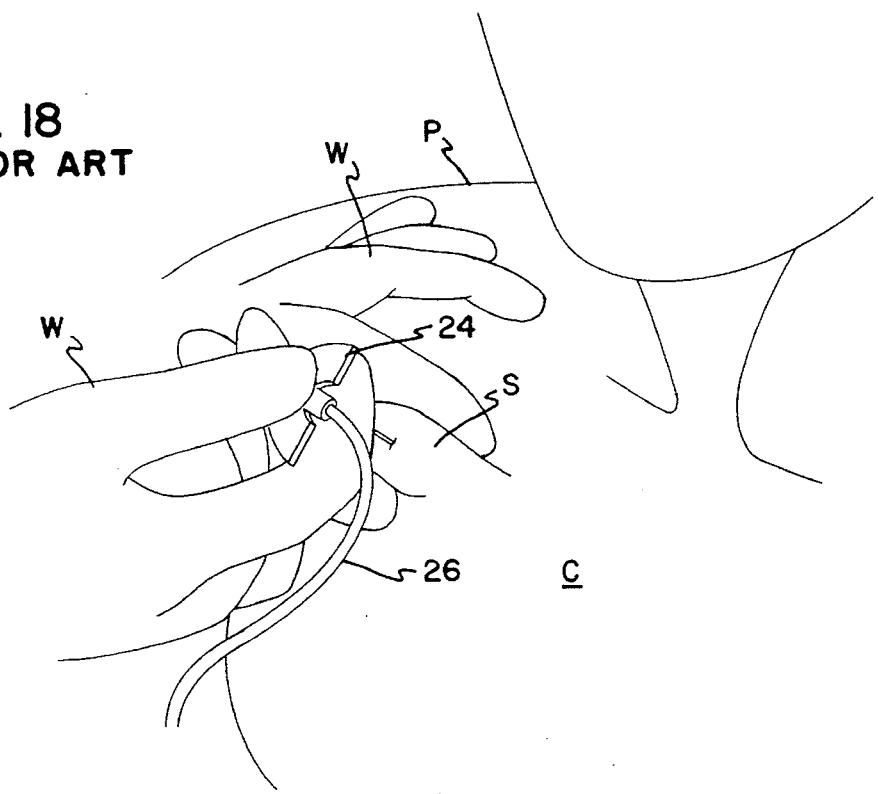
FIG. 18 is a perspective view showing access to the implantable venous access device with a needle having extension tubing attached thereto.

Now, referring to FIGS. 9 and 10, the protector 70 comprises a ring 72 and a shroud 74. The ring 72 has a central aperture 76 for receiving the septum 16 of the portal 14. The ring 72 is formed from a substantially rigid material, such as a plastic material, having a thickness suitable for providing adequate support to stabilize the patient's skin S and the portal 14.

The shroud 74 is joined to the ring 72, originating about the periphery of the central aperture 76 and extending radially a predetermined distance from the central aperture 76 overtop the ring 72. The shroud 74 is formed from a pliable, puncture resistant material, such as a thick vinyl material. The purpose of the shroud 74 is to protect the hand of the health care worker W against needle strikes while inserting a needle 24.

The ring 72 and the shroud 74 further have a mutually aligning, radially extending, discontinuous regions 78. These regions 78 provide passages for the extension tubing 36 of the needle 24 therethrough, thus enabling the protector 70 to be removed after the needle 24 has been inserted.

In use, the portal 14 is located and the ring 72 is applied over the portal 14 such that the septum 16 is received in the central aperture 76, thus stabilizing the both the patient's skin S and the portal 14. With the ring 72 in position and the shroud 74 covering the hand of the health care worker W holding the ring 72, the needle 24 may be easily inserted into the septum 16 without assuming the risk of a needle strike.

To further reduce the risk of accidental needle strikes, the needle guard 80, as is shown in FIGS. 11 through 14, is provided to minimize the exposure of the needle 24 prior to its use. The needle guard 80 comprises an elongated, deformable barrel 82 a bore 84 passing therethrough. A progressively separable, longitudinal slit 86 is provided in the wall of the barrel 82 which originates at the lower end of the barrel 82 and extends a majority the length of the barrel 82 to terminate a predetermined distance from an upper end. An opening 88 passes through the barrel 84 at the terminal end of the slit 84. As is clearly shown in FIG. 11, the needle 24 is received by the opening 88 and the barrel 82. Upon insertion of the needle 24 into the patient's skin S, the slit 84 is progressively separated until the needle 24 is completely inserted, at which point the needle guard 80 is shed entirely from the needle 24.

It should be noted that the needle guard 80 may further include a thin webbing 90 along the slit 84 for maintaining the slit 84 in a closed posture. Henceforth, the slit 84 provides an easement for rupturing the webbing 90 upon the displacement of the needle 24.

It is to be understood that the present invention is not limited to the embodiments described above, but encompasses any and all embodiments within the scope of the following claims.

I claim:

1. A method of handling a needle comprising the steps of:

providing a body construction defining an accessible interior, the body construction having a self-closing passageway adjacent to a first end of the body construction, the body construction having a cover with a stop surface adjacent to a second end of the body construction, the cover defining an opening to the accessible interior;

positioning the first end of the body construction adjacent to a needle having a tip inserted into an implanted portal;

passing an end of a needle grasping tool through the opening and then through the self-closing passageway;

grasping the needle with the needle grasping tool while the needle grasping tool is positioned in the opening and the self-closing passageway;

pulling the needle with the needle grasping tool to remove the needle from the portal;

pulling the needle with the needle grasping tool past the self-closing passageway;

releasing the needle in the interior of the body construction between the self-closing passageway and the stop surface of the cover; and removing the needle grasping tool from the interior of the body construction.

2. The method of claim 1, further comprising the step of rotating the cover relative to the first end of the body construction prior to removing the needle from the portal.

3. The method of claim 1, further comprising the steps of:

providing the body construction with a notch at the first end; and positioning a tubing attached to the needle in the notch prior to removing the needle from the portal.

4. The method of claim 1, wherein the needle and the portal are received in a recess of the body construction before removal of the needle from the portal when the first end of the body construction is positioned adjacent to the needle.

5. A method of handling a needle having a tip inserted into a portal implanted under a patient's skin, the method comprising the steps of:

provinding a needle grasping tool having a portion extending through a self-closing passageway of a needle handing device;

grasping the needle with the needle grasping tool extending through the self-closing passageway of the needle handling device;

pressing the needle handling device against the patient's skin;

pulling the needle with the needle grasping tool to remove the needle from the portal while the needle handling device is pressed against the patient's skin; and pulling the needle with the needle grasping tool past the self-closing passageway and into an enclosed chamber of the needle handling device.

6. The method of claim 5, further comprising the step of releasing the needle positioned in the enclosed chamber from the needle grasping tool.

7. The method of claim 5, further comprising the step of positioning a tubing attached to the needle in a notch of the needle handling device adjacent to the patent's skin before the needle is removed from the portal.

8. A method of handling a needle comprising the steps of:

providing a needle grasping tool having a portion extending through a self-closing passageway of a needle handing device;

grasping the needle with the needle grasping tool extending through the self-closing passageway of the needle handling device;

pulling the needle with the needle grasping tool past the self-closing passageway and into an enclosed chamber of the needle handling device; and releasing the needle positioned in the enclosed chamber from the needle grasping tool.

* * * * *